(12) United States Patent
Umasankar et al.

(10) Patent No.: US 10,712,306 B2
(45) Date of Patent: Jul. 14, 2020

(54) SENSOR FOR DETECTION OF ACETONE

(71) Applicants: Yogeswaran Umasankar, Homestead, FL (US); Shekhar Bhansali, Weston, FL (US); Ahmed Hasnain Jalal, Miami, FL (US); Neera Bhansali, Weston, FL (US)

(72) Inventors: Yogeswaran Umasankar, Homestead, FL (US); Shekhar Bhansali, Weston, FL (US); Ahmed Hasnain Jalal, Miami, FL (US); Neera Bhansali, Weston, FL (US)

(73) Assignee: The Florida International University Broad of Trustees, Miami, FL (US)

( * ) Notice: Subject to any disclaimer, the term of this patent is extended or adjusted under 35 U.S.C. 154(b) by 0 days.

(21) Appl. No.: 16/582,230

(22) Filed: Sep. 25, 2019

(65) Prior Publication Data

US 2020/0103366 A1    Apr. 2, 2020

Related U.S. Application Data

(60) Provisional application No. 62/739,737, filed on Oct. 1, 2018.

(51) Int. Cl.
*G01N 27/407*    (2006.01)
*G01N 27/406*    (2006.01)
(Continued)

(52) U.S. Cl.
CPC ....... *G01N 27/4065* (2013.01); *G01N 27/301* (2013.01); *G01N 27/407* (2013.01);
(Continued)

(58) Field of Classification Search
CPC .......................... G01N 27/407; G01N 33/0047
See application file for complete search history.

(56) References Cited

U.S. PATENT DOCUMENTS

| | | | | |
|---|---|---|---|---|
| 3,703,696 A | * | 11/1972 | Browall | G01N 27/121 338/35 |
| 4,735,661 A | * | 4/1988 | Hollander | G01K 1/143 136/232 |

(Continued)

OTHER PUBLICATIONS

Jalal et al., "A Model for Safe Transport of Critical Patients in Unmanned Drones with a 'Watch' Style Continuous Anesthesia Sensor," Journal of The Electrochemical Society, 165 (8) B3071-B3077 (2018) (Year: 2018).*

(Continued)

*Primary Examiner* — Alexander S Noguerola
(74) *Attorney, Agent, or Firm* — Saliwanchik, Lloyd & Eisenschenk

(57) ABSTRACT

Continuous monitoring of acetone is a challenge using related art sensing methods. Though real-time detection of acetone from different biofluids is promising, signal interference from other biomarkers remains an issue. A minor fluctuation of the signals in the micro-ampere range can cause substantial overlapping in linear/polynomial calibration fittings. To address the above in non-invasive detection, principal component analysis (PCA) can be used to generate specific patterns for different concentration points of acetone in the subspace. This results in improvement of the problem of overlapping of the signals between two different concentration points of the data sets while eliminating dimensionality and redundancy of data variables. An algorithm following PCA can be incorporated in a microcontroller of a sensor, resulting in a functional wearable acetone sensor. Acetone in the physiological range (0.5 ppm to 4 ppm) can be detected with such a sensor.

17 Claims, 6 Drawing Sheets

(51) Int. Cl.
*G01N 33/64* (2006.01)
*G01N 27/417* (2006.01)
*G01N 27/30* (2006.01)
*G01N 33/00* (2006.01)

(52) U.S. Cl.
CPC ....... *G01N 27/417* (2013.01); *G01N 33/0047* (2013.01); *G01N 33/64* (2013.01)

(56) References Cited

U.S. PATENT DOCUMENTS

2017/0184537 A1* 6/2017 Umasankar ........ G01N 27/4074
2019/0246958 A1* 8/2019 Moeller ............... A61B 5/4845

OTHER PUBLICATIONS

Product specification for Texas Instruments HDC1080 Digital Humidity Sensor with Temperature Sensor, unpaginated, 2016 (Year: 2016).*

* cited by examiner

SENSOR FOR DETECTION OF ACETONE

CROSS-REFERENCE TO A RELATED APPLICATION

This application claims the benefit of U.S. Provisional Application Ser. No. 62/739,737, filed Oct. 1, 2018, which is hereby incorporated by reference herein in its entirety, including any figures, tables, and drawings.

STATEMENT OF GOVERNMENT SUPPORT

This invention was made with government support under Award No. EEC-1160483 awarded by the National Science Foundation Nanosystems Engineering Research Centre for Advanced Self-Powered Systems of Integrated Biosensors and Technologies (ASSIST). The government has certain rights in the invention.

BACKGROUND

Ketogenesis is a natural catabolic process that takes place in the liver through the breakdown of fatty acids into ketone bodies (KBs). Three different KBs generated in this metabolic process include: i) acetoacetate; ii) β-hydroxy butyrate; and iii) acetone. The generation of ketone bodies is different in a healthy person compared to a hyperglycemic or type-1 diabetic patient (e.g., the breath ketone level of a healthy person and a diabetic patient varies for example within ranges of 0.3-0.9 ppm and >1.8 ppm, respectively). For a type-1 diabetic patient, the pancreas produces an insufficient amount of insulin. A high level of insulin suppresses the rate of ketogenesis and a lower amount of insulin can lead to an increase of ketone bodies in blood, including glucose. No direct relationship has been established yet between ketone and glucose generation, though it is evident that both glucose and KBs are at elevated levels for hyperglycemic patients. The elevated level of KBs turns the blood acidic, which is the most serious hyperglycemic emergency in patients with type 1 diabetes, referred to as "diabetic ketoacidosis" (DKA). Elevated levels of ketone can also be generated due to starvation, exercise, or alcohol consumption; nonetheless, DKA is the most severe case as the ketone levels can more than double. Moreover, it can critically affect the heart, muscles, the respiratory system, the gastrointestinal system, and/or the central nervous system and can result in a coma or death.

The existing methods for measuring ketones include point of care and laboratory blood tests, urine tests by chemical strips, and lung ketone analysis by breath analyzers. In the blood tests, β-hydroxy butyrate is monitored, and in the breath tests acetone is monitored. Blood testing is an invasive test while acetone monitoring from urine and breath are both noninvasive. Unfortunately, these methods do not monitor ketone levels continually and alert the subject if a dangerous state of DKA occurs. It is life threatening if DKA occurs while the patient is asleep.

In addition, existing standalone organic volatile sensors are incapable of specifically detecting a single specific volatile organic compound in a multi-dimensional environment. The non-specific detection of the existing sensors generates false positives and false negatives. It is noted that multi-dimensional environments are common and exist in all biological fluids and vapors.

BRIEF SUMMARY

Embodiments of the subject invention provide novel and advantageous sensors, sensing platforms, and methods of sensing for the detection of acetone. A sandwiched structure of a membrane electrode assembly (MEA) can be used for a proton exchange membrane fuel cell (PEMFC) sensor for real-time monitoring of acetone. The sensor can include three electrodes (rather than two) to achieve signal stability. A multivariate statistical technique, such as principal component analysis (PCA), can be used to reduce the redundancy and dimensionality of data sets and can be employed on data sets to improve the precision of calibration by the generation of a unique cluster for each concentration in the subspace. The device can be functionalized by following an algorithm (e.g., based on PCA) and fit any unknown concentration on the cluster.

Electrochemical sensors have typically been found to be most suitable for long term sensing. Among them, fuel cell sensors offer simplicity, long working lifetime, scalability, and portability, and they therefore can be used in breathalyzers and for transdermal measurement of specific volatile compounds (e.g. alcohol). Though such sensors show relatively better accuracy and selectivity, there is a possibility of false readings due to interferent compounds or the dependency of the sensor on different ambient parameters, such as humidity, pressure, and temperature, for its function. Multivariate analysis is a strong tool to resolve these issues for precision of measurement and classification. The most common multivariate statistical techniques are independent component analysis (ICA), PCA, linear discriminant analysis (LDA), cluster analysis, and partial least squares analysis (PLS). Any of these can be used in embodiments of the subject invention.

Calibration results of embodiments of the subject invention show that the sensor displays linearity with a significant coefficient of determinant (96.1%) within the physiological range (0.5 ppm to 4 ppm). This parameter cannot on its own ensure the reliability of the measurement in the multivariate environment in real life. As precision is vital for DKA detection, a small fluctuation of signal in the sub-micro ampere (sub-$\mu A$) range due to interference from other compounds or parametric dependency on ambient variables (e.g., relative humidity, temperature, pressure) can cause significant overlapping in calibration fittings. PCA reduces the redundancy and dimensionality of data sets and can be employed on data sets to improve the precision of calibration by the generation of a unique cluster for each concentration in the subspace. The device can be functionalized by following an algorithm based on PCA and fit any unknown concentration on the cluster. The data from embodiments of the subject invention enable patients, their health care advisor(s), and their family to monitor the condition in real time, uncover DKA episodes, alert them, and monitor treatment efficacy. Embodiments of the subject invention provide an improvement over related art sensors, most of which suffer from instability, non-linearity, cross-selectivity, inaccuracy at low concentrations, and lack of portability.

In an embodiment, a sensor for detection of acetone can comprise: a proton exchange membrane (PEM); a working electrode on a first surface of the PEM; a reference electrode on the first surface of the PEM; and a counter electrode on a second surface of the PEM in a position corresponding to that of the working electrode, the first surface of the PEM being opposite to the second surface of the PEM. A surface area of the working electrode on the first surface of the PEM can be greater than a surface area of the counter electrode on the second surface of the PEM and a surface area of the reference electrode on the first surface of the PEM. A shortest distance between the working electrode and the reference electrode on the first surface of the PEM, measured in a first direction parallel to the first surface of the PEM, being at least three times greater than a thickness of the PEM, measured in a thickness direction perpendicular to the first direction. The sensor can further comprise a processor and a machine readable medium (at least one of which can be in operable communication with at least one of the electrodes of the sensor) comprising instructions stored thereon that, when executed by the processor, perform a multivariate statistical technique on data obtained from at least one of the working electrode, the counter electrode, and the reference electrode. The multivariate statistical technique can be, for example, PCA, and can include the following steps: (i) standardizing the data; (ii) obtaining eigenvectors and eigenvalues (d) from a covariance or correlation matrix of the data; (iii) sorting the eigenvalues in descending order and choosing the eigenvectors that correspond to the k largest eigenvalues, where k is the number of dimensions of a new feature subspace (k≤d); iv) multiplying the received data and the eigenvectors to obtain a new data set; v) re-orientating the new data set onto new axes of a plot to obtain a re-oriented data set; and vi) plotting the re-oriented data set on the plot.

In another embodiment, a sensor device can comprise: a substrate; a micro-fuel cell sensor disposed on a first surface of the substrate; at least one humidity sensor disposed on the substrate; and at least one thermocouple disposed on the substrate, and the first surface of the substrate can have a surface area of, for example, 100 square millimeters ($mm^2$) or less. The sensor device can further comprise a processor and a machine readable medium (at least one of which can be in operable communication with the micro-fuel cell sensor) comprising instructions stored thereon that, when executed by the processor, perform a multivariate statistical technique on data obtained from the micro-fuel sensor. The multivariate statistical technique can be, for example, PCA, and can include the following steps: (i) standardizing the data; (ii) obtaining eigenvectors and eigenvalues (d) from a covariance or correlation matrix of the data; (iii) sorting the eigenvalues in descending order and choosing the eigenvectors that correspond to the k largest eigenvalues, where k is the number of dimensions of a new feature subspace (k≤d); iv) multiplying the received data and the eigenvectors to obtain a new data set; v) re-orientating the new data set onto new axes of a plot to obtain a re-oriented data set; and vi) plotting the re-oriented data set on the plot.

DETAILED DESCRIPTION

Figure 1A:
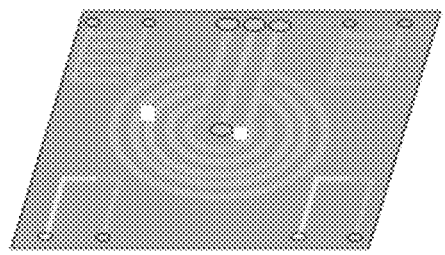
FIG. 1(a) is a schematic view of a micro-fabricated single sensor platform enabled with sensor fusion technology.

Embodiments of the subject invention provide novel and advantageous sensors, sensing platforms, and methods of sensing for the detection of acetone. A sandwiched structure of a membrane electrode assembly (MEA) can be used for a proton exchange membrane fuel cell (PEMFC) sensor for real-time monitoring of acetone. The sensor can include three electrodes (rather than two) to achieve signal stability. A multivariate statistical technique, such as principal component analysis (PCA), can be used to reduce the redundancy and dimensionality of data sets and can be employed on data sets to improve the precision of calibration by the generation of a unique cluster for each concentration in the subspace. The device can be functionalized by following an algorithm (e.g., based on PCA) and fit any unknown concentration on the cluster.

Electrochemical sensors have typically been found to be most suitable for long term sensing. Among them, fuel cell sensors offer simplicity, long working lifetime, scalability, and portability, and they therefore can be used in breathalyzers and for transdermal measurement of specific volatile compounds (e.g. alcohol). Though such sensors show relatively better accuracy and selectivity, there is a possibility of false readings due to interferent compounds or the dependency of the sensor on different ambient parameters, such as humidity, pressure, and temperature, for its function. Multivariate analysis is a strong tool to resolve these issues for precision of measurement and classification. The most common multivariate statistical techniques are independent component analysis (ICA), PCA, linear discriminant analysis (LDA), cluster analysis, and partial least squares analysis (PLS). Any of these can be used in embodiments of the subject invention.

Calibration results of embodiments of the subject invention show that the sensor displays linearity with a significant coefficient of determinant (96.1%) within the physiological range (0.5 ppm to 4 ppm). This parameter (coefficient of determinant) cannot on its own ensure the reliability of the measurement in the multivariate environment in real life. As precision is vital for DKA detection, a small fluctuation of signal in the sub-micro ampere (sub µA) range due to interference from other compounds or parametric dependency on ambient variables (e.g., relative humidity, temperature, pressure) can cause significant overlapping in calibration fittings. PCA reduces the redundancy and dimensionality of data sets and can be employed on data sets to improve the precision of calibration by the generation of unique cluster for each concentration in the subspace. The device can be functionalized by following an algorithm based on PCA and fit any unknown concentration on the cluster. The data from embodiments of the subject invention enable patients, their health care advisor(s), and their family to monitor the condition in real time, uncover DKA episodes, alert them, and monitor treatment efficacy. Embodiments of the subject invention provide an improvement over related art sensors, most of which suffer from instability, non-linearity, cross-selectivity, inaccuracy at low concentrations, and lack of portability.

In many embodiments, a sensor can include three electrodes, and the three electrodes of the sensor can include a working electrode (WE), a counter electrode (CE), and a reference electrode. Materials for the electrodes can be any suitable material known in the art. For example, nickel 400 (monel) can be used for the WE and CE, and platinum clad (Pt-clad) niobium can be used as the RE.

In many embodiments, three-electrode fuel cell sensors can be employed for analyte sensing (e.g., acetone sensing) in a miniaturized platform. For the precise and reliable measurement of an analyte (e.g., acetone) within the physiological range, principal component analysis can be employed. As discussed in Example 1, PCA has been successfully implemented for the isolation of each cluster representing specific concentration in the data subspace. Although the linear fitting showed good sensitivity (0.246 µA/ppm/cm$^2$) and linearity (R2=96.1%), it was difficult to separate signals for the small change of concentration. The PCA improves the classification of different concentrations in the subspace and generates a unique pattern for each concentration of acetone in the data spectrum. Referring again to Example 1, variances of −1.3238, −0.4671, and 1.0245×10$^{-9}$ were obtained and inferred the control of first (73.92%) and second (26.08%) principal components in the data sets. As this pattern is unique for acetone, it improves also the selectivity in a multivariate environment.

In an embodiment, a miniaturized wearable fuel cell sensing platform can be used for acetone detection and can operate in a low power mode. Such a low power mode can result in a battery time of at least 4 days (e.g., about 4.33 days, or even more) without the need to recharge. The miniaturized wearable fuel cell sensing platform can include a three-electrode fuel cell sensor as described herein.

Advantages of embodiments of the subject invention include, but are not necessarily limited to, the following: 1) accurate detection of acetone compounds in a multi-dimensional environment; 2) detection of ketoacidosis during a hyperglycemic emergency; 3) autonomous analysis and evaluation of the signals obtained from the sensor network; 4) sensor nodes operation control as required for the selective detection of desired volatile organic compounds; and 5) false positive and false negative signal elimination or reduction in volatile organic compound sensors, compared with related art sensors.

Figure 1B:
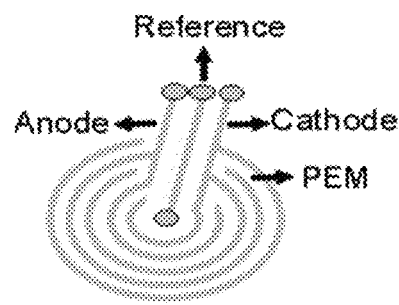
FIG. 1(b) is a schematic view of a coiled micro-fuel cell sensor.
Figure 1C:
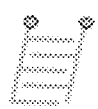
FIG. 1(c) is a schematic view of a micro-humidity sensor.
Figure 1D:
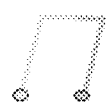
FIG. 1(d) is a schematic view of a micro-thermocouple.
Figures 2A, 2B:
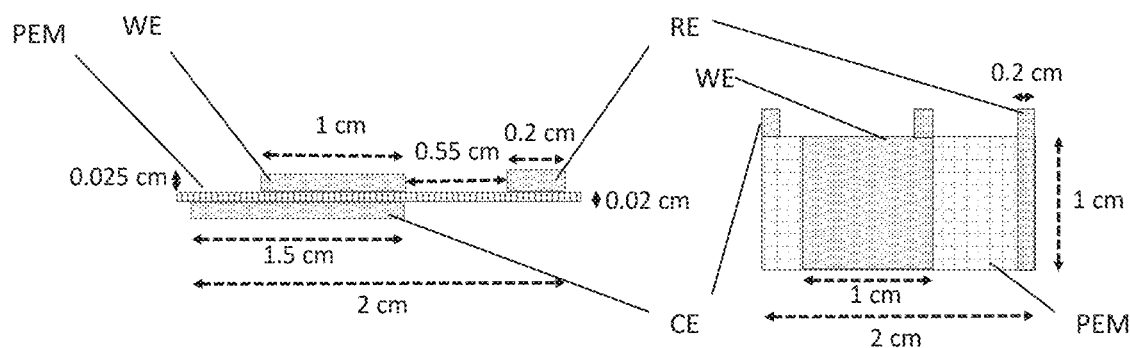
FIG. 2(a) shows a cross-sectional view of a three-electrode fuel cell sensor according to an embodiment of the subject invention. The dimensions shown are for exemplary purposes and should not be construed as limiting.
FIG. 2(b) shows a top view of a three-electrode fuel cell sensor according to an embodiment of the subject invention. The dimensions shown are for exemplary purposes and should not be construed as limiting.

In many embodiments, specific detection can be achieved with the help of a sensor fusion concept, where three different sensors are fabricated into a single platform, as shown in FIG. 1, along with algorithms to autonomously analyze and evaluate the signals. The sensor platform can include, for example, a silicon wafer or a glass substrate, and all three miniaturized structures (micro-fuel cell, humidity sensor, and thermocouple) can be contained within, e.g., a 9×9 millimeter (mm) dimension. The surface of the substrate having the miniaturized structures disposed thereon can have a surface area of, for example, 200 mm$^2$ or less, 150 mm$^2$ or less, 100 mm$^2$ or less, 90 mm$^2$ or less, 85 mm$^2$ or less, 81 mm$^2$ or less, 75 mm$^2$ or less, or 60 mm$^2$ or less. The substrate can be any suitable material known in the art, and silicon and glass are mentioned only for exemplary purposes. The sensor fusion device can include the micro-fuel cell, which can include an anode, a cathode, a reference electrode, and a PEM as shown in FIG. 1(b). The sensor fusion device can further include at least one humidity sensor (depicted in FIG. 1(c)) and/or at least one thermocouple (depicted in FIG. 1(d)). Referring to FIG. 1(a), in one embodiment, the sensor fusion device can include a micro-fuel sensor in a central area of the substrate, two humidity sensors in two respective corners of the substrate and two thermocouples on two other respective corners of the substrate. The micro-fuel cell, humidity sensor(s), and thermocouple(s) can all be formed on the same surface of the substrate, and their respective lower surfaces can all be coplanar with each other. The micro-fuel cell can be the micro-fuel cell sensor as depicted in FIGS. 2(a) and 2(b).

Bio-sensing is a simpler process in a controlled environment, but it becomes complex in a multidimensional environment. No single related art biosensor can be used independently to draw conclusions in the multidimensional environment. The existing biosensors present in wearable and point-of-care devices work independently so they lack the capability to accurately diagnose, unless it's a controlled environment. In bio-sensing, a blood test is one example of a controlled measurement. Sweat, breath, and transdermal analysis are examples of multidimensional environment measurements, because these samples contain a multitude of components that may interfere with the biosensor signal. Certain embodiments of the subject invention can use the data from multiple biosensors and sensors to accurately diagnose the subject. One such example is the detection of ketoacidosis during a hyperglycemic emergency through breath, sweat, or transdermal analysis. Ketoacidosis may take place due to a hyperglycemic emergency situation or because of fat burning during a heavy workout. Existing biosensors in this category will not identify the difference between ketoacidosis due to a hyperglycemic emergency situation or because of a heavy workout. Certain embodiments of the subject invention can include a gyroscope, accelerometer, and/or global position system sensor to determine the above-mentioned difference.

For accurate detection of ketoacidosis through a fuel cell sensor, two different problems need be addressed, as follows.

1. Identifying an interference signal due to humidity, because of the micro-fuel cell sensor signal dependence on the humidity signal. For breath analysis, U.S. Pat. No. 7,992,422 refers to fuel cells, employing an open circuit voltage (OCV) method for the calibration of acetone. It has been found that OCV data varies with respect to time based on changing the humidity, temperature, and amount of moisture absorbed by the solid-state electrolyte membrane. Therefore, the variation of the reference potential value causes false positive readings to detect a specific concentration in a huge margin.
2. Identifying the cause for ketoacidosis, because it occurs in two different occasions: (i) during a serious diabetic condition; and (ii) during a heavy workout.

Regarding problem 1, a humidity reading from a humidity sensor network placed in close proximity to the micro-fuel cell sensor environment can be used and measured. The humidity entangled signal can then be computed and subtracted from the micro-fuel cell data. Similarly, the temperature dependence of the micro-fuel cell sensor can also be calibrated with the help of a thermocouple.

Regarding problem 2, activity of the user can be monitored through one or more motion sensors, and then the computed calories burnt data can be used as a feedback loop for a micro-fuel cell sensor. Two scenarios are involved in this computation: (1) if the micro-fuel cell sensor detects ketone while the motion sensor is idle (i.e., the user is inactive, sleeping, etc.), it can be concluded as a DKA situation; and (ii) if the micro-fuel cell sensor detects ketone while the motion sensor is active (i.e., the user is active physically, then it shows ketones are not due to DKA). In both these solutions, a statistical model can be obtained from the collecting of data of all the sensors to calibrate ketone/acetone signals within the physiological range. Employing this pattern recognition technique and algorithm, the sensing unit can be capable of detecting precise and accurate levels in blood in a noninvasive method. The system can create an opportunity for implementing a multiple biosensor network in wearable and point-of-care devices reliably and independently.

Monitoring the potential change in the anode (working electrode) with high accuracy is important for constructing a reliable acetone fuel cell sensor. In principle, acetone diffusing from the epidermis interacts with the fuel cell sensor anode, which is present in close proximity to the skin (e.g., in direct physical contact with the skin or very close thereto (e.g., within 2 inches or less)). The humid acetone vapor gets oxidized on the anode to form protons, electrons, and formic acid. During this electrochemical reaction, the protons are exchanged to the cathode through the PEM. Simultaneously, the atmospheric oxygen gets reduced to water in the presence of protons and eight electrons. The reaction mechanism of the fuel cell type acetone sensor for continuous monitoring is as given in [2] and [3] below in Example 1. The two-electrode system also has the same electrochemical reaction mechanism as mentioned above. The problem in measuring full cell reaction is the interference from the cathode, where the byproduct water and humidity will affect both the current and potential output of the sensor. Thus, to eliminate the signal interference, the three-electrode system can be used. The advantage of the three-electrode system is that it helps monitor only the anode (half-cell) reaction, which can be achieved by measuring the potential between the anode (working electrode) and the reference electrode, and letting the current pass between the anode and the cathode (counter electrode). This mechanism gives a very stable signal of the acetone oxidation in the anode.

Embodiments of the subject invention also include methods of detecting an analyte (e.g., acetone) by using a sensor or sensor device as described herein.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the embodiments of the subject invention. They are, of course, not to be considered as limiting the invention. Numerous changes and modifications can be made with respect to embodiments of the invention.

Example 1

Materials and Methods
Chemicals and Apparatus

For the electrode materials of a three electrode fuel cell, the following were used: nickel 400 (monel) was used for the working electrode (WE) and counter electrode (CE), and platinum-clad (Pt-clad) niobium was used for the reference electrode (RE). A noncorrosive monel sheet with a thickness of 0.05 cm was purchased from M. Vincent and Associates Ltd. and nonwoven Pt-clad niobium mesh was purchased from Technic Inc. Perforation and laser cutting of the WE and CE (monel sheet) were performed at SBC industries in Miami. Nafion115 (thickness of 0.0127 cm) from Ion Power was used for the proton exchange membrane (PEM). Sulfuric acid (95%), acetone (95.27%), isopropanol (IPA, 95.27%), and hydrogen peroxide ($H_2O_2$) were purchased from Sigma-Aldrich, Fisher Scientific Inc., and Alfa Aesar, respectively. The aqueous solutions were prepared with de-ionized (DI) water.

A vacuum oven (Model 280A) was purchased from Fisher Scientific. A hydraulic hot press (model 2100 from PHI) was used to prepare the sandwiched structure of the fuel cell sensor. For the electrochemical experiments, a potentiostat from CHI 1230B having MC470 was used. A 3D printer (model: Replicator2 from Makerbot) was employed for the chamber design of the experiments.

Design of Three Electrode Micro-Fuel Cell

The dimensions of the WE, CE, and RE were considered (1 cm×1 cm×0.05 cm), (1 cm×1.5 cm×0.05 cm), and (1 cm×0.2 cm×0.05 cm), respectively, of the micro-fuel cell (the cross-sectional and top views are shown in FIG. 2a and FIG. 2b, respectively). The electrolyte membrane, Nafion (2 cm×1 cm×0.0127 cm) was sandwiched in between the electrodes to form the membrane exchange assembly (MEA). Because the CE is the primary current collector, the overall area of this electrode was designed to be substantially larger than the WE and RE. In contrast, the area of the RE was designed to contain the smallest surface area and it was placed near to the WE on the same side of the membrane. The distance between the RE and WE (L=0.55 cm) was maintained to be greater than three times (L/δ>3) the membrane thickness (δ) to avoid the asymmetrical current distribution and potential variation on WE due to edging effect. That is, the distance between WE and the RE, measured in a direction parallel to the surface of the PEM on which they are disposed, can be at least three times the thickness of the PEM. The WE was placed on the opposite side of the CE in such a way that maximum area of WE was overlapped with that of CE (FIG. 2a).

Fabrication of Micro-Fuel Cell Sensor

The monel sheet was perforated and cut according to the design that was created at SolidWorks CAD tool. After laser cutting, micro-porous monel sheet was cleaned thoroughly with detergent, DI water, and isopropanol (IPA) in an ultrasound bath for 5 minutes each. Prior to hot pressing of the MEA, Nafion115 was treated with 3% $H_2O_2$ aqueous solution at 60° C. for an hour to oxidize organic impurities. Consequently, the Nafion was rinsed with boiling DI water repeatedly. Then it was boiled in 0.5 M diluted $H_2SO_4$ for an hour to remove metallic impurities at 60° C. for an hour. Immediately, it was rinsed with DI water and dried in an oven at 100° C. for 24 hrs.

A mold was designed using SolidWorks CAD tool for hot pressing. The sandwich structure of three electrodes fuel cell was achieved by placing them inside the mold according to design. Subsequently, the MEA was hot pressed at 75° C. and 2500 psi for 10 minutes by the hydraulic press. The fabricated fuel cell was kept at room temperature for 1-2 hours inside the mold and it was observed that the electrodes adhere properly with the membrane through this thermal cycling process. Before the experiments, a constant relative humidity was maintained for each sensor, by treating the sensors in a humidified chamber for 30 minutes at 24° C. and atmospheric pressure.

Significance of Three Electrodes Micro-Fuel Cell System

Figure 2C:
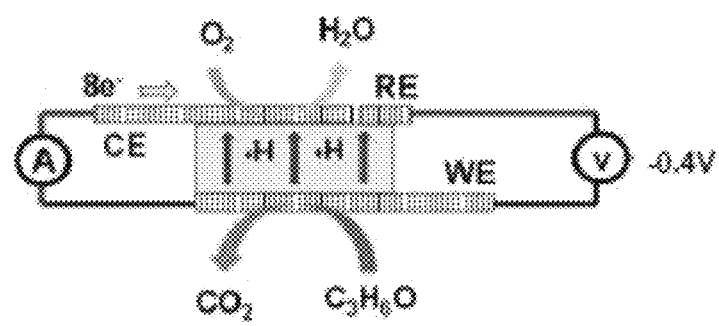
FIG. 2(c) shows the mechanism for acetone detection and its amperometric measurement according to the sensor of FIGS. 2(a) and 2(b).

Contrary to the two-electrode system in a traditional fuel cell setup, a three-electrode setup can be used in embodiments of the subject invention. The two-electrode systems also have the same electrochemical reaction mechanism as mentioned above. The advantage of the three-electrode system is that it helps monitor only the WE (half-cell) reaction in the presence of acetone, which can be achieved by biasing a potential between the WE and RE, and allows only the faradic current pass between the WE and CE. For accurate acetone detection, it is necessary to measure the faradic oxidation current on the working electrode instead of the full cell current. Due to high impedance between the RE and WE, the electrons will only flow unidirectionally towards the CE (as shown in FIG. 2c) because the standard potential ($E_0$) causes an attractive electromotive force (E) following the Nernst equation:

$$E = E_0 - \frac{RT}{nF}\ln Q_r \quad [1]$$

where n is the number of electron, F is the Faraday constant, R is the universal gas constant, T is absolute temperature, and $Q_r$ is the redox reaction quotient.

The three-electrode fuel cell system for amperometric measurement is a combination of galvanic and electrolytic cells. The mechanism of electrons flowing from the WE to CE follows galvanic cell principle. To promote oxidation in the presence of acetone, a negative potential (−0.4 V) was selected as a biasing potential between the RE and WE following the electrolytic cell principle as shown in FIG. 2c. In this three-electrode fuel cell system, a high impedance is maintained between the WE and RE, so that the faradic current can only pass in between the WE and CE, avoiding polarization of the RE. This design ensures only the measurement of current from the CE to WE and provides a stable signal.

Working Mechanism of Fuel Cell Acetone Sensor

Monitoring the potential change in the WE with high accuracy is important for constructing a reliable acetone fuel cell sensor. In principle, acetone diffusing from the epidermis interacts with the WE of the fuel cell sensor that is present in proximity to the skin. The acetone vapor gets oxidized on the WE to generate protons, electrons, carbon dioxide, and formic acid. During this electrochemical reaction, the protons penetrate through the proton exchange membrane (PEM) and accumulate at the CE. Instantaneously, or nearly instantaneously, the atmospheric oxygen gets reduced to water in the presence of protons and electrons. These eight electrons come from the WE through the external connection. The reaction mechanism of the fuel cell type acetone sensor for continuous monitoring is given in [2] and [3], and shown in FIG. 2c.

$$C_3H_6O + 3H_2O \rightarrow 8H^+ + 8e^- + CH_3COOH + CO_2 \quad [2]$$

$$2O_2 + 8H^+ + 8e^- \rightarrow 4H_2O \quad [3]$$

For the calibration, a three-electrode fuel cell sensor was placed in a 3D printed chamber in such a way that the WE was exposed to acetone vapor and the CE was exposed to atmospheric oxygen at 24° C. Acetone evaporated from the solution due to the partial pressure following Henry's formula as follows:

$$\frac{\text{Concentration of acetone in the liquid solution}}{\text{Concentration of acetone in the gaseous state}} = K_{w/a} \quad [4]$$

Here, $K_{w/a}$ is the "Ostwald partition coefficient". If a diluted acetone solution is brought to equilibrium to air, the partial pressure of acetone in the vapor phase is a function of the system temperature (24° C.) and the acetone concentration in liquid phase. Different concentrations of acetone were exposed to the WE of the fuel cell during the measurement following this principle.

Results

Linear Calibration Fit for Acetone Detection

Figure 3A:
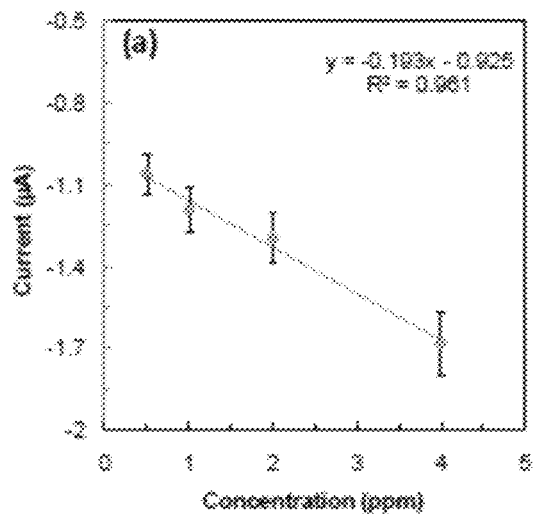
FIG. 3(a) shows a plot of current versus concentration in a linear calibration fitting for a three-electrode proton exchange membrane fuel cell (PEMFC) sensor.
Figure 3B:
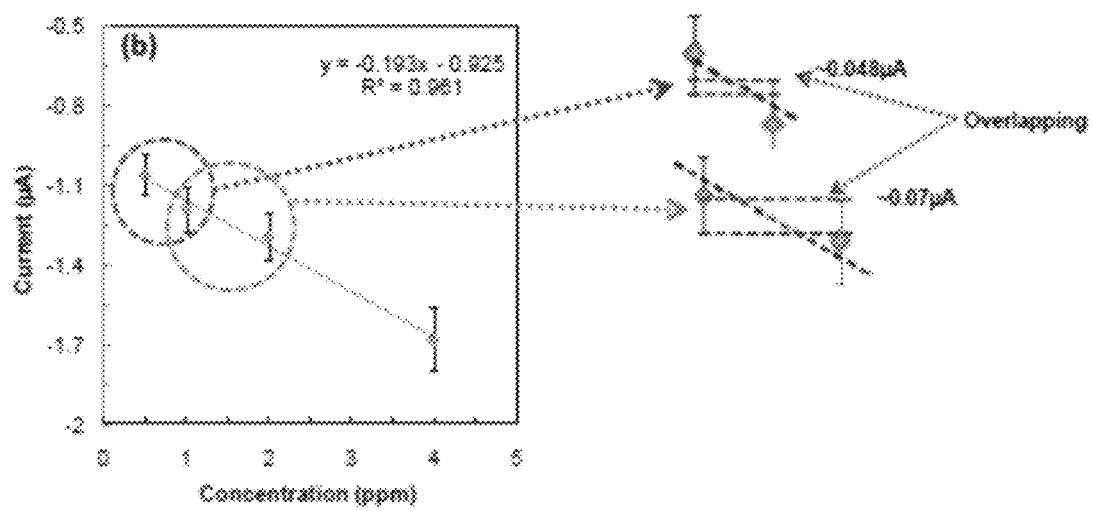
FIG. 3(b) shows signal overlapping between different concentration points in the linear calibration of FIG. 3(a).

Four different concentrations within the physiological range—0.5 ppm, 1 ppm, 2 ppm, and 4 ppm—were measured for the calibration. The concentration versus current plot, shown in FIG. 3a, validates that the sensor could maintain a sensitivity of 0.246 µA ppm$^{-1}$ cm$^{-2}$ with a minimum concentration level of 0.5 ppm. The limit of detection (LoD)

was calculated as 1.91 ppm from this measurement and the response time was monitored 10-20 seconds. The coefficient of determinant (R2) of 96.1% supports the linearity of the acetone sensing of the fuel cell sensor. However, excellent linearity and good sensitivity do not ensure the reliability of the calibration within the physiological range of acetone detection. The magnification of each data point (in FIG. 3b) reveals that there was a significant overlap of the signals between different concentrations. Due to higher standard deviations, reliability in sub-ppm level of detection was impeded. For example, the overlapping between 0.5 ppm to 1 ppm and 1 ppm to 2 ppm are determined as 0.048 µA and 0.07 µA, respectively. The standard deviation (SD) and relative standard deviation (RSD) values of current from Table 1 support this argument for all measured concentrations.

TABLE I

SD and RSD values of different data points from concentration vs. current plot

|  | Concentration (ppm) | | | |
| --- | --- | --- | --- | --- |
|  | 0.5 | 1 | 2 | 4 |
| Standard deviation (µA) | 0.07 | 0.13 | 0.05 | 0.21 |
| Relative standard deviation (RSD, %) | 7.08 | 10.62 | 3.7 | 12.43 |

Repeatability of the Sensor

Figure 4:
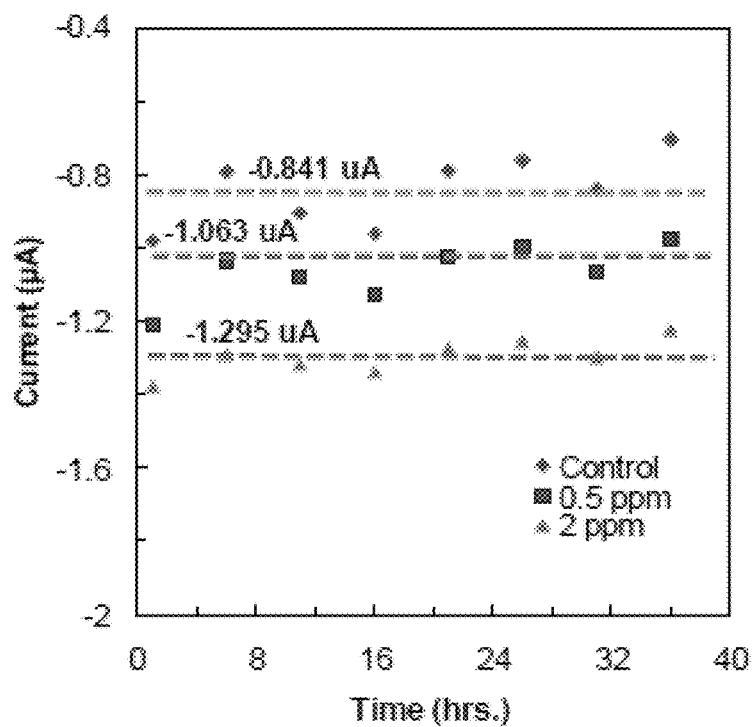
FIG. 4 shows a plot of current versus concentration in a repeatability test of a sensor for 0 ppm (control) (diamond data points and top fitted line), 0.5 ppm (square data points and middle fitted line), and 2 ppm (triangle data points and bottom fitted line).

For the repeatability test, the fuel cell sensor was exposed to acetone vapor at two different concentrations—0.5 ppm and 2 ppm—eight different times. A comparison was drawn with the control (0 ppm) signals with these concentrations in FIG. 4. The ranges of the data set for these three concentrations were calculated 0.27 µA, 0.23 µA, and 0.15 µA, correspondingly. Similarly, the averages were also calculated as −0.84 µA, −1.06 µA, and −1.29 µA, and the maximum signal drifts from the average were about 0.14 µA, 0.15 µA, and 0.08 µA, respectively. As the range of the data set for each concentration is wide, and the maximum and standard deviations are large, the signals are overlapping in a large margin during measurement.

PCA for Selective Diagnosis of DKA

PCA was applied on the above-mentioned data by the following steps: (i) standardizing the data; (ii) obtaining the eigenvectors and eigenvalues (d) from the covariance or correlation matrix; and (iii) sorting eigenvalues in descending order and choose the eigenvectors that correspond to the k largest eigenvalues, where k is the number of dimensions of the new feature subspace (k≤d). For a response matrix X, each element $x_{ij}$ concerns the $j^{th}$ measurement value for the $i^{th}$ considered data where the kth principal component is noted as $PC_k$:

$$PC_k = \Sigma_{i=1}^{n} \alpha_{ik} x_{ij} \quad [5]$$

where n is the number of variables and $\alpha_{ik}$ is the eigenvector for the $i^{th}$ variable. PCA followed three steps to execute its processing: i) multiplication was executed between the original data and the eigenvectors; ii) re-orientation of this data set onto the new axes; and iii) plotting the oriented data.

In the PCA analysis, three response variables—steady state current (Iss), difference of steady state current from reference point (ΔI), and gradient of current with respect to time (dI/dt)—were considered. A 32×3 matrix was created in the total data set, which is fragmented into 4 sub-datasets and each sub-dataset (represent each concentration) contained an 8×3 matrix. The mean of each dataset was governed and standardized. A covariance matrix was developed for those two variables and the eigenvectors (V) were determined from this matrix. The eigenvalues were generated as −1.3238, −0.4671, and 1.0245×10$^{-9}$, respectively. Because the eigenvalue of the third component is very low, the two principal components (k=2) were considered in this case and the number of dimensions of the principal components is k=2 in the subspace. The data variances of the first and second principal components were identified as 73.92% and 26.08%, respectively. The final datasets were plotted after the standardization of the eigenvectors' data, as shown in FIG. 5.

Figure 5:
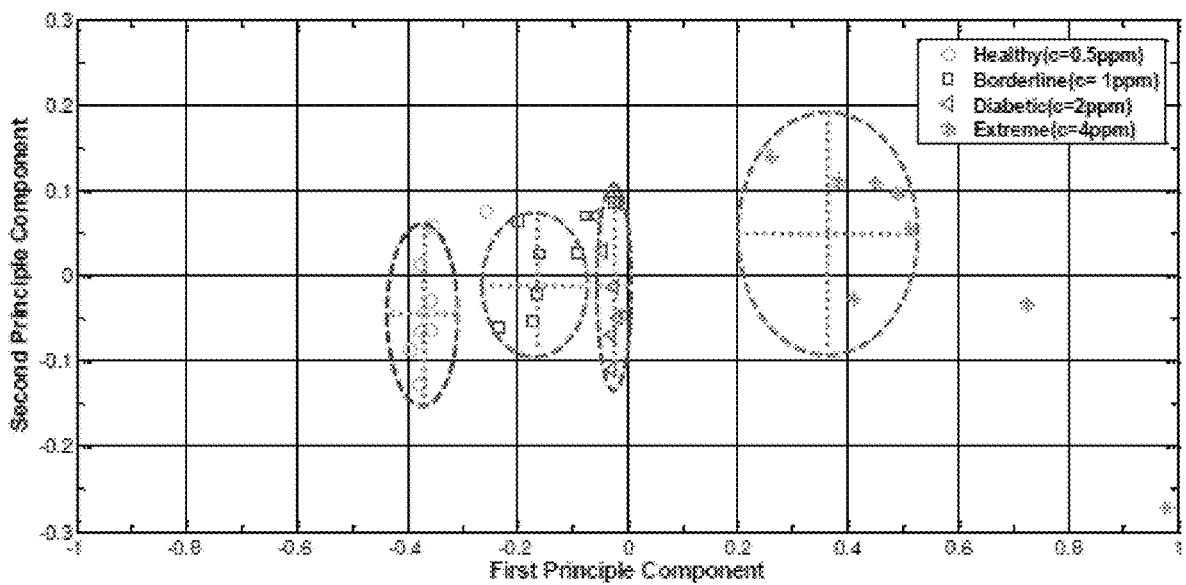
FIG. 5 shows results for a principal component analysis of four different concentrations of acetone. The left-most grouping (circular data points) is for a concentration of 0.5 ppm; the second-to-the-left grouping (square data points) is for a concentration of 1 ppm; the second-to-the-right grouping (triangular data points) is for a concentration of 2 ppm; and the right-most grouping (asterisk data points) is for a concentration of 4 ppm.

Referring to FIG. 5, results show that data can be separated into four different clusters (healthy=0.5 ppm, borderline=1 ppm, diabetic=2 ppm, and extreme=4 ppm). It is observed that PCA removed the redundancy and the dimensionality of the data points that was clearly visible in linear calibration plot. It was also evident that each cluster has a maximum of two outliers, which were created because of different independent variables. The possible independent factors can be listed as: (i) membrane water content variation; (ii) electrode surface fouling; (iii) membrane degradation over time; (iv) temperature variation; and (v) atmospheric pressure fluctuation. It was also clear that the data of the highest concentration group (4 ppm) were more dispersed than the other groups along the PC1 and PC2 axis, which supported the argument regarding the better sensitivity in favor of the lower concentration. As the variance of the first principal component is as high as 73.92%, PC1 has more control than PC2, even though the separation between the clusters is distinguishable.

Overall, the clusters (concentrations of acetone) corresponding to healthy, borderline, diabetic, and extreme diabetic cases were clearly distinguishable from the subspace.

Example 2—Wearable Platform for Acetone Sensing

A comprehensive wearable platform with a miniaturized potentiostat was developed for a sustainable solution for acetone detection. A customized printed circuit board (PCB) was designed to accommodate the low cost potentiostat (LMP91000) with a low power data processing microcontroller (nRF51822) and Bluetooth (RN-42) for the data transmission. The device uses nRF51822 from Nordic semiconductor as an integrated wireless microcontroller with Bluetooth low energy (BLE) capabilities to provide wireless communication and peripheral controls. The working mechanism of LMP91000 is known.

The device begins amperometric operation when it detects a voltage less than −0.05 V across the sensor electrodes (RE and WE). The amperometric current detected corresponds to the concentration of acetone, which can be determined through calibration. The current from LMP91000 is converted to a potential and fed to the internal analog-to-digital converter (ADC) of the wireless microcontroller. This information is then sent wirelessly via Bluetooth to a device, such as smartphone, which can send the data to the cloud.

Calibration of acetone for detection in human subjects presents a challenge as the signal suffers through many interferents. The algorithm for precise calibration requires computational power, which is taxing on both devices used. Therefore, the calibration algorithm for precise results can be done on the cloud once the data is uploaded. This saves battery power and comparatively limited computational power over the device and phone. Power consumption of the device depends on: i) run time current drawn from the CPU; ii) BLE transmission and communication; and iii) LMP91000's amperometric operation. Because most of these operations only occur for a short period, the modules that run them can be pushed to a lower power state, thereby reducing power consumption. The CPU runs for a short time during BLE transmission and ADC conversion of analog output from LMP91000. The remaining time can be utilized by the CPU to run other peripheral operations consuming about 2.6 µA at a lower power. LMP91000, while in amperometric mode, consumes an average current of about 7.95 µA over the time with a total uptime of 39%. Including about 5 µA for cell conditioning, the current for this sensor is calculated as 9.75 µA with the LMP in "stand mode" for 60% of the time. Using a 3.7 V and 365 mAh battery, the operational lifetime of the system can be more than 4 days (e.g., up to 4.33 days, or even more in some cases).

Example 3

Specific detection can be achieved with the help of a sensor fusion concept, where three different sensors are fabricated into a single platform, as shown in FIG. 1, along with algorithms to autonomously analyze and evaluate the signals. Such a sensor platform was fabricated using a silicon wafer, and all three miniaturized structures (micro-fuel cell, humidity sensor, and thermocouple) were contained within a 9×9 mm dimension. Among these miniaturized structures, the thermocouple was constructed with two metals, chromium (Cr) and aluminum (Al) with the overall dimension being 2×1.6 mm. As shown in FIG. 1d, one side of the thermocouple was made by Cr and the other side was by Al, and they overlap each other at the terminals, forming a 'U' shape structure. Both the micro-fuel cell and humidity sensors were interdigitated electrodes made of gold with a dimension 78 mm$^2$ and 2×1.6 mm, respectively (FIG. 1). The gaps between the interdigitated electrodes of the micro-fuel cell were filled with a proton exchange membrane (Nafion). Similarly, the gap between the electrodes in the humidity sensor was coated with a suitable photoresist polymer (for example, SU8).

To derive the relationships between the variables in sensing, preliminary studies were carried out in controlled environments using multiple individual sensors (not sensor fusion system). Then the data from each sensor were plotted to understand the relationships. One such example discussed below is the relationship between the humidity variable in the acetone/ketone sensing. The sensor used for acetone was a miniaturized fuel cell sensor, and a commercially available humidity sensor.

Fabrication of Fuel Cell Sensor (Type 1):

Because the counter electrode (CE) is the primary current collector in a fuel cell, the overall area of the CE was maintained to be larger than that of the working electrode (WE) and the reference electrode (RE). In contrast, the area of the RE was the smallest to avoid the current conduction during operation. To optimize the edging effect, the RE was placed 0.55 centimeters (cm) away from the WE on the Nafion membrane side. The MEA was assembled placing the electrolyte membrane, Nafion (2 cm×1 cm), between the electrodes by placing the counter electrode opposite to the WE, as shown in FIGS. 2a and 1b. The dimension of the working (anode), counter (cathode), and reference electrodes were 1 cm×0.8 cm, 1 cm×1 cm, and 1.5 cm×0.2 cm, respectively. The sandwich structure of the MEA was obtained using the hot press at 75° C. and 2500 psi for 10 minutes.

FIGS. 2a and 2b show the structure of the fuel cell based sensor and its cross section. The middle layer with the squares in the same figure represents the proton exchange membrane (PEM or Nafion membrane). Contrary to a traditional fuel cell two-electrode system, three electrodes were developed to monitor the signals. The three-electrode systems are advantageous compared to the two-electrode system. For example, the electrochemical potential measurement in a two-electrode system (anode and cathode) will show the full cell reaction potential, whereas using a three electrode system the half-cell potential can be measured. The three-electrode system was constructed in such a way that working and reference electrodes were placed at the same side of the PEM (FIGS. 2a and 2b). This design facilitates monitoring the anodic reaction of the fuel cell sensor.

Figure 6:
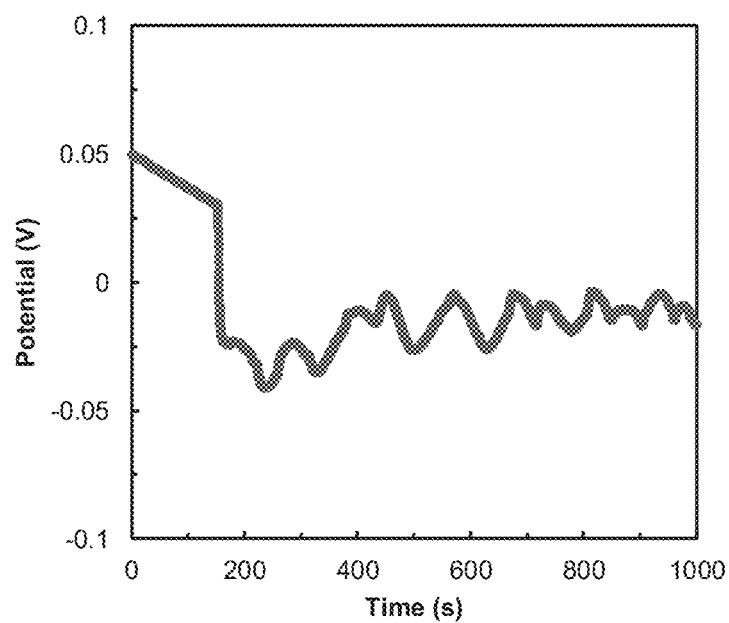
FIG. 6 shows open circuit voltage (OCV) of a fuel cell sensor in the presence of acetone (10 μl of 15.6 M), measured for 1000 seconds of exposure time. The plot shows voltage (in Volts) versus time (in seconds).

Fuel Cell Response to Acetone:

Open circuit voltage (OCV) shows unique characteristics of each compound for a particular catalyst electrode. However, OCV varies within a certain potential window with respect to time, as shown in FIG. 6. The variation was because of the change in H$^+$ ions content of the PEM, which leads to an error in the measurements. It is observed that even for identical electrodes, the OCV signal varies in the millivolt (mV) range. Therefore, to reduce the effect of humidity, the sensor was exposed to humidity for 30 minutes at 24° C. under room temperature before the experiments. The OCV response of the fuel cell in presence of acetone (10 µl of 15.6 M) was monitored over a period of 1000 seconds in a closed chamber. The sensor attained its steady state after 150 seconds; however, there was noise in the signal with ±20 mV. As time increased, the noise reduced to ±3 mV (FIG. 6). From these experiments, the average potential window of acetone oxidation was identified in the range of −25 mV to −40 mV.

Figure 7:
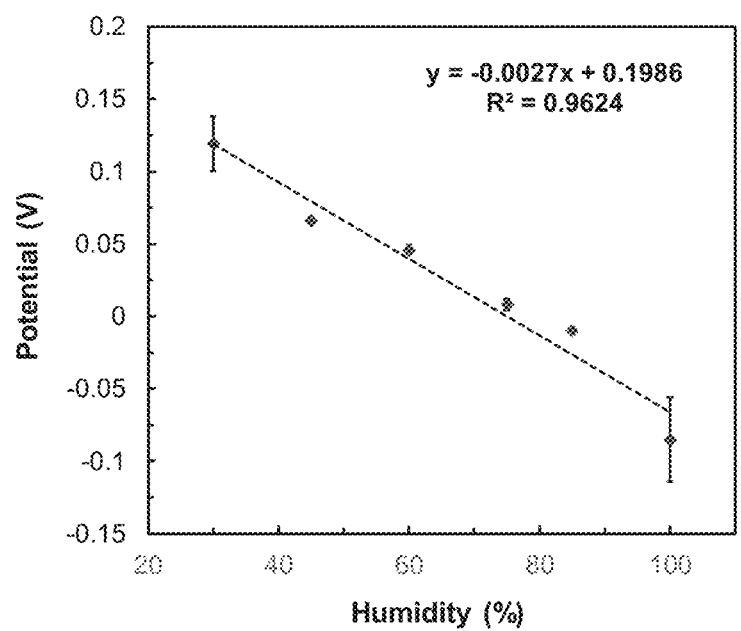
FIG. 7 shows a plot representing the effect of humidity (%) on the OCV of the micro fuel cell sensor in the absence of acetone. The plot shows voltage (in Volts) versus humidity (in %).

Relationship Between OCV and Humidity:

To understand the effect of humidity on the OCV of the fuel cell sensor, controlled experiments in the presence of various percentages of humidity were carried out and plotted (FIG. 7). The results show that the OCV varies linearly with the percent change in humidity %. The rate of change was 2.7 mV for each percentage decrease in humidity at room temperature (24° C.). In a multidimensional environment, humidity varies inconsistently, which significantly affects the sensor reading. Hence, a sensor fusion method with pattern recognition method (e.g., implemented via a processor or controller executing code for an algorithm) can be advantageous. The sensor fusion technique of embodiments of the subject invention is capable of deriving a relationship between humidity level, temperature, and the acetone signal generation towards precise calibration in a multidimensional environment.

Figure 8:
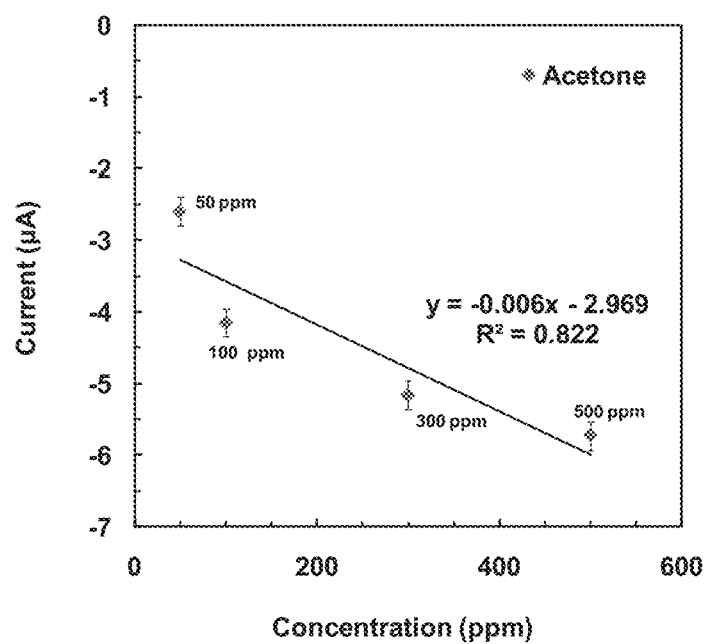
FIG. 8 shows a linear calibration plot of a fuel cell sensor, for various concentrations of acetone. The concentrations of acetone are labeled on the plot, which shows current (in μA) versus concentration of acetone (in parts per million (ppm)).

Linear Regression Studies of the Fuel Cell Sensor:

Four different concentrations were tested. The sensor was operated at 44% humidity at 24° C., at −0.3 V biasing potential. The concentration versus current plot is shown in FIG. 8, which shows the sensor response from 50 ppm to 500 ppm with a sensitivity of −7.64 nA-ppm$^{-1}$ cm$^{-2}$. However, the response is not linear, having an R$^2$ value of 0.822. To overcome these calibration issues, a pattern recognition method, such as PCA, can be considered. This was explained in more detail in Example 1.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

What is claimed is:

1. A sensor for detection of acetone, the sensor comprising:
   a proton exchange membrane (PEM);
   a working electrode on a first surface of the PEM;
   a reference electrode on the first surface of the PEM; and
   a counter electrode on a second surface of the PEM in a position corresponding to that of the working electrode,
   the first surface of the PEM being opposite to the second surface of the PEM,
   a surface area of the working electrode on the first surface of the PEM being greater than a surface area of the counter electrode on the second surface of the PEM and a surface area of the reference electrode on the first surface of the PEM.

2. The sensor according to claim 1, a surface area of the counter electrode on the second surface of the PEM being greater than a surface area of the reference electrode on the first surface of the PEM.

3. The sensor according to claim 1, the PEM being formed of Nafion.

4. The sensor according to claim 1, a shortest distance between the working electrode and the reference electrode on the first surface of the PEM, measured in a first direction parallel to the first surface of the PEM, being at least three times greater than a thickness of the PEM, measured in a thickness direction perpendicular to the first direction.

5. The sensor according to claim 1, further comprising a processor and a machine readable medium comprising instructions stored thereon that, when executed by the processor, perform a multivariate statistical technique on data obtained from at least one of the working electrode, the counter electrode, and the reference electrode.

6. The sensor according to claim 5, the multivariate statistical technique being principle component analysis (PCA), independent component analysis (ICA), linear discriminant analysis (LDA), cluster analysis, or partial least squares analysis (PLS).

7. The sensor according to claim 5, the multivariate statistical technique being PCA.

8. The sensor according to claim 7, the performing of the PCA comprising:
   (i) standardizing the data;
   (ii) obtaining eigenvectors and eigenvalues (d) from a covariance or correlation matrix of the data;
   (iii) sorting the eigenvalues in descending order and choosing the eigenvectors that correspond to the k largest eigenvalues, where k is the number of dimensions of a new feature subspace (k≤d);
   iv) multiplying the received data and the eigenvectors to obtain a new data set;
   v) re-orientating the new data set onto new axes of a plot to obtain a re-oriented data set; and
   vi) plotting the re-oriented data set on the plot.

9. A sensor for detection of acetone, the sensor comprising:
   a proton exchange membrane (PEM);
   a working electrode on a first surface of the PEM;
   a reference electrode on the first surface of the PEM; and
   a counter electrode on a second surface of the PEM in a position corresponding to that of the working electrode,
   the first surface of the PEM being opposite to the second surface of the PEM,
   the working electrode being formed of nickel, the reference electrode comprising niobium, and the counter electrode being formed of nickel.

10. A sensor device, comprising:
    a substrate;
    a micro-fuel cell sensor disposed on a first surface of the substrate;
    at least one humidity sensor disposed on the substrate; and
    at least one thermocouple disposed on the substrate,
    the first surface of the substrate having a surface area of 100 square millimeters (mm2) or less,
    the micro-fuel sensor comprising a working electrode, a reference electrode, a counter electrode, and a proton exchange membrane (PEM),
    the at least one humidity sensor comprising a first humidity sensor formed at a first corner on the first surface of the substrate and a second humidity sensor formed at a second corner on the first surface of the substrate,
    the at least one thermocouple comprising a first thermocouple formed at a third corner on the first surface of the substrate and a second thermocouple formed at a fourth corner on the first surface of the substrate, and
    the micro-fuel cell sensor being disposed on a central region of the first surface of the substrate.

11. The sensor device according to claim 10, further comprising a processor and a machine readable medium comprising instructions stored thereon that, when executed by the processor, perform a multivariate statistical technique on data obtained from the micro-fuel sensor.

12. The sensor device according to claim 11, the multivariate statistical technique being principle component analysis (PCA), independent component analysis (ICA), linear discriminant analysis (LDA), cluster analysis, or partial least squares analysis (PLS).

13. The sensor device according to claim 12, the multivariate statistical technique being PCA, and
    the performing of the PCA comprising:
    (i) standardizing the data;
    (ii) obtaining eigenvectors and eigenvalues (d) from a covariance or correlation matrix of the data;
    (iii) sorting the eigenvalues in descending order and choosing the eigenvectors that correspond to the k largest eigenvalues, where k is the number of dimensions of a new feature subspace (k≤d);
    iv) multiplying the received data and the eigenvectors to obtain a new data set;
    v) re-orientating the new data set onto new axes of a plot to obtain a re-oriented data set; and
    vi) plotting the re-oriented data set on the plot.

14. The sensor device according to claim 10, each thermocouple of the at least one thermocouple comprising a U-shape structure with a first side formed of chromium and a second side formed of aluminum, and
    each humidity sensor of the at least one humidity sensor comprising interdigitated electrodes formed of gold.

15. The sensor device according to claim 10, the first surface of the substrate having a length of no more than 9 mm and a width of no more than 9 mm, such that a surface area of the first surface of the substrate is 81 mm2 or less.

16. A sensor device, comprising:
    a substrate;
    a micro-fuel cell sensor disposed on a first surface of the substrate;
    at least one humidity sensor disposed on the substrate; and
    at least one thermocouple disposed on the substrate, the first surface of the substrate having a surface area of 100 square millimeters (mm2) or less,
the micro-fuel cell sensor comprising:
  a PEM;
  a working electrode on a first surface of the PEM;
  a reference electrode on the first surface of the PEM; and
  a counter electrode on a second surface of the PEM in a position corresponding to that of the working electrode, the first surface of the PEM being opposite to the second surface of the PEM,
a surface area of the working electrode on the first surface of the PEM being greater than a surface area of the counter electrode on the second surface of the PEM and a surface area of the reference electrode on the first surface of the PEM, and
a surface area of the counter electrode on the second surface of the PEM being greater than a surface area of the reference electrode on the first surface of the PEM.

17. A sensor device, comprising:
a substrate;
a micro-fuel cell sensor disposed on a first surface of the substrate;
at least one humidity sensor disposed on the substrate; and
at least one thermocouple disposed on the substrate,
the first surface of the substrate having a surface area of 81 square millimeters (mm2) or less,
the sensor device further comprising a processor and a machine readable medium comprising instructions stored thereon that, when executed by the processor, perform a multivariate statistical technique on data obtained from the micro-fuel sensor,
the multivariate statistical technique being principle component analysis (PCA),
the performing of the PCA comprising:
(i) standardizing the data;
(ii) obtaining eigenvectors and eigenvalues (d) from a covariance or correlation matrix of the data;
(iii) sorting the eigenvalues in descending order and choosing the eigenvectors that correspond to the k largest eigenvalues, where k is the number of dimensions of a new feature subspace (k≤d);
iv) multiplying the received data and the eigenvectors to obtain a new data set;
v) re-orientating the new data set onto new axes of a plot to obtain a re-oriented data set; and
vi) plotting the re-oriented data set on the plot,
each thermocouple of the at least one thermocouple comprising a U-shape structure with a first side formed of chromium and a second side formed of aluminum,
each humidity sensor of the at least one humidity sensor comprising interdigitated electrodes formed of gold,
the micro-fuel cell sensor comprising a working electrode, a reference electrode, a counter electrode, and a proton exchange membrane (PEM),
the at least one humidity sensor comprising a first humidity sensor formed at a first corner on the first surface of the substrate and a second humidity sensor formed at a second corner on the first surface of the substrate,
the at least one thermocouple comprising a first thermocouple formed at a third corner on the first surface of the substrate and a second thermocouple formed at a fourth corner on the first surface of the substrate, and
the micro-fuel cell sensor being disposed on a central region of the first surface of the substrate.

* * * * *

UNITED STATES PATENT AND TRADEMARK OFFICE
CERTIFICATE OF CORRECTION

PATENT NO. : 10,712,306 B2
APPLICATION NO. : 16/582230
DATED : July 14, 2020
INVENTOR(S) : Yogeswaran Umasankar et al.

Page 1 of 1

It is certified that error appears in the above-identified patent and that said Letters Patent is hereby corrected as shown below:

On the Title Page

Item (73) "Assignee: The Florida International University Broad of Trustees" should read
--Assignee: The Florida International University Board of Trustees--.

Signed and Sealed this
Twenty-seventh Day of July, 2021

Drew Hirshfeld
*Performing the Functions and Duties of the
Under Secretary of Commerce for Intellectual Property and
Director of the United States Patent and Trademark Office*